(12) United States Patent
Garcia Molina

(10) Patent No.: US 9,993,610 B2
(45) Date of Patent: Jun. 12, 2018

(54) BRAIN-WAVE BASED CLOSED-LOOP SENSORY STIMULATION TO INDUCE SLEEP

(71) Applicant: KONINKLIJKE PHILIPS N.V., Eindhoven (NL)

(72) Inventor: Gary Nelson Garcia Molina, Madison, WI (US)

(73) Assignee: Koninklijke Philips N.V., Eindhoven (NL)

( * ) Notice: Subject to any disclaimer, the term of this patent is extended or adjusted under 35 U.S.C. 154(b) by 306 days.

(21) Appl. No.: 14/758,579

(22) PCT Filed: Jan. 9, 2014

(86) PCT No.: PCT/IB2014/058134
§ 371 (c)(1),
(2) Date: Jun. 30, 2015

(87) PCT Pub. No.: WO2014/118654
PCT Pub. Date: Aug. 7, 2014

(65) Prior Publication Data
US 2015/0343168 A1    Dec. 3, 2015

Related U.S. Application Data

(60) Provisional application No. 61/757,776, filed on Jan. 29, 2013.

(51) Int. Cl.
*A61M 21/02*    (2006.01)
*A61M 21/00*    (2006.01)

(52) U.S. Cl.
CPC ..... *A61M 21/02* (2013.01); *A61M 2021/0022* (2013.01); *A61M 2021/0027* (2013.01);
(Continued)

(58) Field of Classification Search
CPC .. A61M 2021/0022; A61M 2021/0027; A61M 2021/0044; A61M 2021/0072;
(Continued)

(56) References Cited

U.S. PATENT DOCUMENTS

2009/0192556 A1    7/2009    Wo et al.
2010/0010289 A1    1/2010    Clare

FOREIGN PATENT DOCUMENTS

CN    202351548 U    7/2012
RU    2271839 C1    3/2006
(Continued)

OTHER PUBLICATIONS

Tononi, "Enhancing Sleep Slow Waves With Natural Stimuli", Investigations and Research, Midecamundi, vol. 54, No. 2, 2010 pp. 82-88.
(Continued)

*Primary Examiner* — Christine H Matthews

(57) ABSTRACT

Systems and methods for delivering stimuli to a subject that prompt the subject to fall asleep use multiple parameters that are based on measured signals related to a patient's brain activity, for example obtained through electroencephalography (EEG). The parameters indicate amplitude in different frequency bands, e.g. high-frequency brain activity and low-frequency brain activity. A stimulus, e.g. auditory stimulus, is delivered to the subject such that the intensity of the stimulus is adjusted based on (changes in) the multiple parameters.

12 Claims, 3 Drawing Sheets

(52) U.S. Cl.
CPC ........... *A61M 2021/0044* (2013.01); *A61M 2021/0072* (2013.01); *A61M 2205/3303* (2013.01); *A61M 2205/50* (2013.01); *A61M 2230/10* (2013.01); *A61M 2230/14* (2013.01); *A61M 2230/40* (2013.01); *A61M 2230/62* (2013.01); *A61M 2230/63* (2013.01)

(58) Field of Classification Search
CPC .......... A61M 21/02; A61M 2205/3303; A61M 2205/50; A61M 2230/10; A61M 2230/14
See application file for complete search history.

(56) References Cited

FOREIGN PATENT DOCUMENTS

| | | |
|---|---|---|
| RU | 2432971 C1 | 11/2011 |
| WO | 2005055802 A2 | 6/2005 |

OTHER PUBLICATIONS

Hoedlmoser et al, "Instrumental Conditioning of Human Sensorimotor Rhythm (12-15 Hz) and Its Impact on Sleep as Well as Declarative Learning" Human Sensorimotor Rhythm, Sleep and Learning, Sleep, vol. 31, No. 10, 2008, pp. 1401-1408.
Bell, "The Use of EEG Theta Biofeedback in the Treatment of a Patient With Sleep-Onset Insomnia", Biofeedback and Self-Regulation, vol. 4, No. 3, 1979, p. 229-236.
Bootzin et al, "Behavioral Techniques and Bi Ofeedback for Insomnia", M.R. Pressman & W.C. Orr, Understanding Sleep: The Evaluation and Treatment of Sleep Disorders, Chapter 16, 1997, pp. 315-338.
Cvetkovic et al, "Sleep Onset Process As an Altered State of Consciousness", States of Consciousness: Experimental Insights Into Meditation, Waking, Sleep and Dreams, Berlin, Germany: Springer, 2011, pp. 157-185.
"Sleep in America" Poll, National Sleep Foundation, 2002, pp. 1-43.

BRAIN-WAVE BASED CLOSED-LOOP SENSORY STIMULATION TO INDUCE SLEEP

CROSS-REFERENCE TO PRIOR APPLICATIONS

This application is the U.S. National Phase application under 35 U.S.C. § 371 of International Application Serial No. PCT/IB2014/058134, filed on Jan. 9, 2014, which claims the benefit of U.S. Application Ser. No. 61/757,776, filed on Jan. 29, 2013. These applications are hereby incorporated by reference herein.

The present disclosure pertains to systems and methods that help a subject to fall asleep, and, in particular, to deliver sensory stimuli that prompt and/or induce a subject to fall asleep.

Sleep and/or sleep quality are related to a person's general health and/or wellbeing. Poor or inadequate sleep is both prevalent and medically undesirable. Above-average delays in falling asleep (or transitioning from wakefulness to a particular sleep stage) may be indicative of sub-optimal sleep patterns and/or habits. The restorative function of sleep may be hindered and/or impaired by problems and/or delays in falling asleep.

Non-drug approaches to sleep onset insomnia include, at least, behavioral approaches, cognitive approaches, and biofeedback approaches. Behavioral approaches include, but are not limited to, sleep hygiene recommendations, stimulus control, sleep restriction, relaxation training and meditation. Cognitive approaches include, but are not limited to, paradoxical intention and cognitive restructuring.

Accordingly, one or more embodiments provide a system configured to deliver stimuli to a subject that prompt the subject to transition into a sleep stage. The system comprises one or more sensors configured to generate one or more output signals conveying information related to one or more parameters associated with brain activity of the subject and one or more processors configured to execute computer program modules. The computer program modules include a parameter determination module and a control module. The parameter determination module is configured to determine a first spectral parameter that indicates power in a first frequency band and a second spectral parameter that indicates power in a second frequency band. The first and second spectral parameters are based on the one or more generated output signals. The average frequency of the first frequency band is higher than an average frequency of the second frequency band. The control module is configured to control a stimulus source to deliver a stimulus to the subject. Controlling the stimulus source includes adjusting an intensity of the stimulus. The adjustment is based on the first spectral parameter and the second spectral parameter.

It is yet another aspect of one or more embodiments to provide a method of delivering stimuli to a subject that prompt the subject to transition into a sleep stage. The method comprises generating one or more output signals conveying information related to one or more parameters associated with brain activity of the subject; determining a first spectral parameter that indicates power in a first frequency band, wherein the first spectral parameter is based on the one or more generated output signals; determining a second spectral parameter that indicates power in a second frequency band, wherein the second spectral parameter is based on the one or more generated output signals, and wherein an average frequency of the first frequency band is higher than an average frequency of the second frequency band; and controlling a stimulus source to deliver a stimulus to the subject by adjusting an intensity of the stimulus, wherein the adjustment is based on the first spectral parameter and the second spectral parameter.

It is yet another aspect of one or more embodiments to provide a system configured to deliver stimuli to a subject that prompt the subject to transition into a sleep stage. The system comprises means for generating one or more output signals conveying information related to one or more parameters associated with brain activity of the subject; means for determining a first spectral parameter that indicates power in a first frequency band, wherein the first spectral parameter is based on the one or more generated output signals; means for determining a second spectral parameter that indicates power in a second frequency band, wherein the second spectral parameter is based on the one or more generated output signals, and wherein an average frequency of the first frequency band is higher than an average frequency of the second frequency band; and means for controlling a stimulus source to deliver a stimulus to the subject by adjusting an intensity of the stimulus, wherein the adjustment is based on the first spectral parameter and the second spectral parameter These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

FIG. 1 schematically illustrates a system to deliver stimuli to a subject that prompt the subject to transition into a sleep stage;

Figure 1:
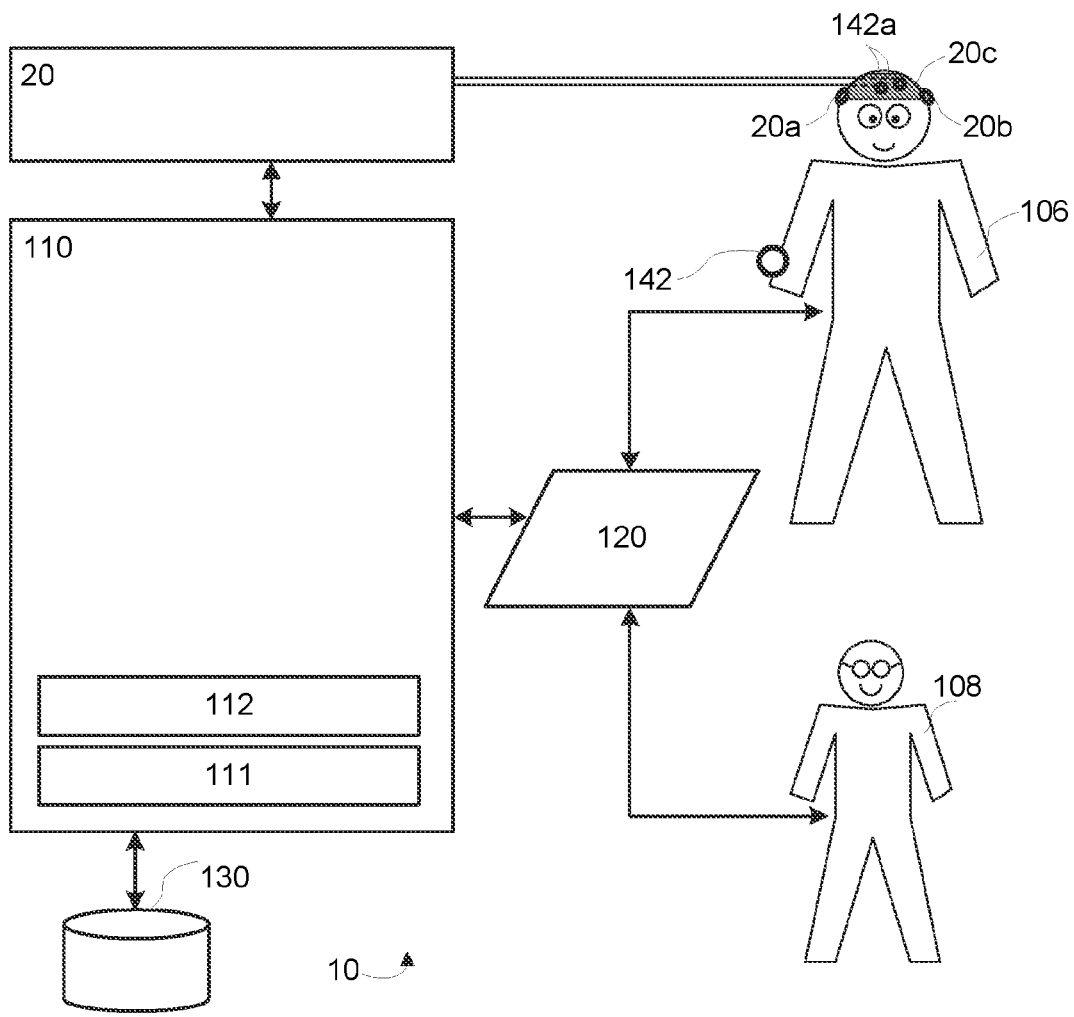

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 to deliver stimuli to a subject 106 that prompt subject 106 to transition into a sleep stage. The sleep stages commonly include a rapid-eye-movement (REM) stage and one or more non-rapid-eye-movement stages (NREMs). Depending on the models and/or definitions used, sleep professionals and/or experts commonly distinguish between three or four different NREM stages. Depending on the definitions used, sleep professionals and/or experts commonly define sleep onset as the transition into the first or second NREM stage. During sleep, subjects commonly alternate between a REM stage and three or four different NREM stages, depending on the models and/or definitions used. NREM stages are usually referred to as stage 1 (N1) through stage 3 (N3). In some embodiments, system 10 may be used to reduce the time it takes for subjects to reach sleep onset, preferably without relying on drugs. System 10 includes one or more of a stimulus source 20, one or more sensors 142, one or more processors 110, a parameter determination module 111, a control module 112, an electronic storage 120, a user interface 120, and/or other components and/or computer program modules.

Sleep onset is associated with various physiological changes, including but not limited to a shift to hypometabolic parasympathetic activity, a decrease in muscle tone activity, heart rate, respiration rate, and skin conductivity, and a shift in brain activity power distribution from higher frequencies to lower frequencies. The power indicated in a frequency band may correspond to the energy in that frequency band, an amplitude in that frequency band, and/or another way to distinguish higher and lower intensity within a frequency band. In some embodiments, the amplitude may pertain to the mean amplitude in a particular frequency band. In some embodiments, the power may be obtained from a power-spectral density estimation using, by way of non-limiting example, the Welch method. In some embodiments, a shift in brain activity may be used, for example in a feedback or closed-loop manner, to control the delivery of stimuli to subject 106. In doing so, subject 106 may perceive changes in the intensity of one or more stimuli. Subject 106 may modulate his/her brain activity, e.g. intentionally through operant conditioning, to adjust the perceived intensity, e.g. to decrease the perceived intensity. Subject 106 may learn how to perform such modulation through operant conditioning, which is a technique in the field of bio-feedback. Bio-feedback approaches to sleep onset insomnia may include, but are not limited to, approaches based on muscle tension and neuro-feedback.

Stimulus source 20 is configured to provide and/or deliver stimuli to subject 106, such as sensory stimuli. Sensory stimuli may include visual stimuli, auditory stimuli, tactile stimuli, olfactory stimuli, electromagnetic stimuli, somatosensory stimuli, other sensory stimuli and/or any combination and/or sequence thereof. Stimulus source may be controlled by control module 112. Stimulus source 20 may be configured such to generate stimuli having an intensity within a range of intensities. For example, for auditory stimuli, the range of intensities may be a range of volume or loudness of the stimuli, such that increased intensity corresponds to louder auditory stimuli. For example, for tactile/haptic stimuli, the range of intensities may be range of amplitude for the movement of a vibration, such that increased intensity corresponds to an increased amplitude for the movement of a vibration. In some embodiments, the intensity of vibration may be related to its frequency, or to both frequency and amplitude.

As used herein, stimuli that are primarily intended for different senses may be referred to as having different modalities. For example, a visual stimulus has a different modality from an auditory stimulus. To some extent, the perception threshold for a particular modality of stimuli may be patient-specific. For example, a particular patient, having exceptional hearing, may have a lower-than-average perception threshold for auditory stimuli. As used herein, the term "perception threshold" refers to a threshold for a measurable reaction or response to a stimulus. The perception threshold may be determined for the state of wakefulness and/or one or more sleep stages of a subject. As such, a subject's perception threshold may be different in different sleep stages. For example, a subject may have different perception thresholds for auditory stimuli depending on the current sleep stage.

Stimulus source 20 may include one or more of a light source, loudspeakers 20a and 20b (e.g. headphones), an electroacoustic transducer, a vibrating component or device, a device or system configured to produce scents, electrodes 142a, and/or other sources of sensory stimuli or transmitters 20b of sensory stimuli. Stimulus source 20 and/or components included or integrated with stimulus source 20, such as, by way of non-limiting example, electrodes 142a, may be embedded and/or combined with a headband 20c, a hat, a helmet, a wristband, and armband, a pillow, a mattress, and/or other objects or combinations of objects that can be worn, used, positioned, and/or carried in proximity of subject 106. For example, a light source may need to be positioned in sufficient proximity such that electromagnetic radiation from the light source can impinge on the eyes, eyelids, and/or face of subject 106 to provide a sensory stimulus to subject 106. In some embodiments, operation of e.g., a loudspeaker 20a included in stimulus source 20 may be adjusted based on the distance between the loudspeaker and subject 106, the level of ambient noise, and/or other environmental considerations, in addition to other considerations described elsewhere herein.

One or more sensors 142 of system 10 in FIG. 1 are configured to generate output signals conveying information related to one or more parameters associated with brain activity of subject 106. Physiological parameters may include parameters related to brain function/activity, such as electroencephalography (EEG), electro-oculography (EOG), parameters related to movement, location, position, tilt, and/or angle of subject 106 and/or a body part of subject 106, respiratory parameters, and/or other parameters. As depicted in FIG. 1, the one or more sensors 142 may include one or more electrodes 142a. Electrodes may operate in multiple modes: in one mode of operation electrodes may be used to generate output signals conveying information related to one or more parameters associated with brain activity of subject 106 (including but not limited to EEG signals). In another mode of operation, electrodes 142 may be used to deliver a stimulus to subject 106, wherein the stimulus may include an electrical stimulus, a sensory stimulus, and/or other types of stimuli that can be delivered through an electrode. In some embodiments, such delivery is controlled by control module 112.

The one or more sensors 142 may include an accelerometer, positional sensor, movement sensor, light sensor, infrared (IR) sensor, electromagnetic sensor, electrode, tilt meter, (video) camera, and/or other sensors. The illustration of sensor 142 including three members in FIG. 1 is not intended to be limiting. In some embodiments, system 10 may use one or more sensors 142. The illustration of the locations of sensors 142 as depicted in FIG. 1 is not intended to be limiting. An individual sensor 142 may be located at or near (a body part of) subject 106, embedded and/or integrated in a pillow, bed, and/or blanket, and/or at other locations. Resulting signals or information from one or more sensors 142 may be transmitted to processor 110, user interface 120, electronic storage 130, and/or other components of system 10. This transmission may be wired and/or wireless.

The illustration of sensor 142 as being separate and distinct from electrodes 142a is not intended to be limiting. In some embodiments, the same one or more electrodes 142a may be used to both provide a stimulus (e.g. in the form of an electrical pulse) and (subsequently) to sense/measure the reaction and/or response of subject 106 to that stimulus.

The one or more sensors 142 may be configured to generate output signals in an ongoing manner, e.g. before, during, and/or after a period of sleep. This may include generating signals intermittently, periodically (e.g. at a sampling period), continuously, continually, at varying intervals, and/or in other ways that are ongoing during at least a portion of period of sleep. The sampling period may be about 0.001 second, 0.01 second, 0.1 second, 1 second, about 10 seconds, about 1 minute, and/or other sampling periods. It is noted that multiple individual sensors 142 may operate using different sampling periods, as appropriate for the particular output signals and/or (frequencies related to particular) parameters derived therefrom. For example, in some embodiments, the generated output signals may be considered as a vector of output signals, such that a vector includes multiple samples of information conveyed related to one or more parameters associated with brain activity. Different parameters may be related to different vectors. A particular parameter determined in an ongoing manner from a vector of output signals may be considered as a vector of that particular parameter.

Figure 2:
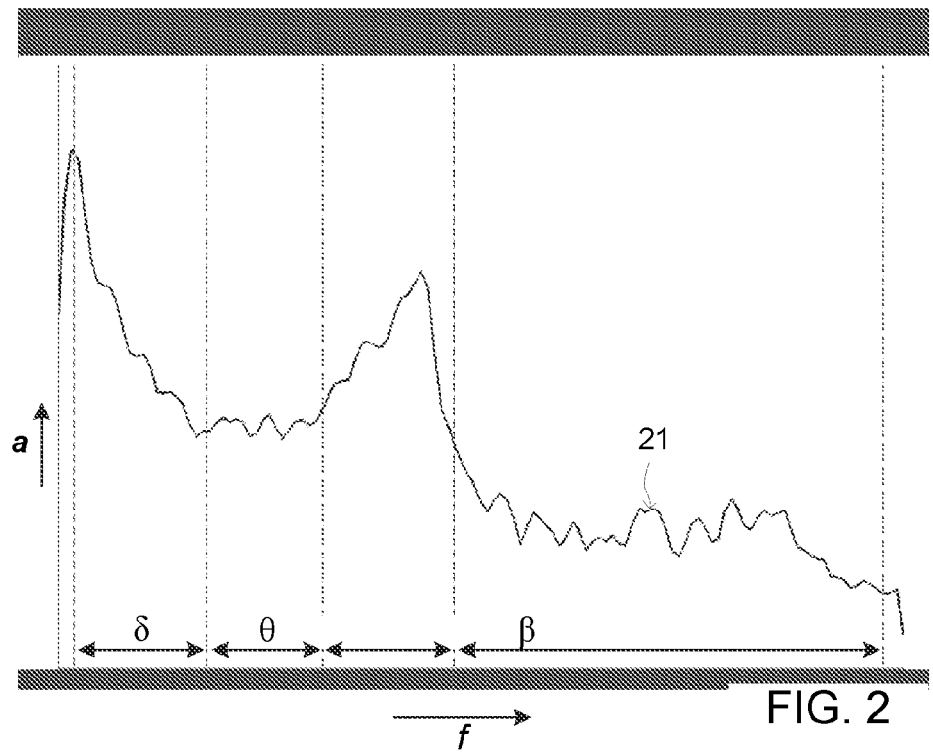
FIG. 2 illustrates a graph depicting amplitudes in different frequency bands of brain activity.

FIG. 2 illustrates a graph 21 depicting amplitudes ("a" on the Y-axis) in different frequency bands ("f" on the X-axis) of brain activity. The amplitude depicted in FIG. 2 may, by way of non-limiting example, correspond to electrical brain activity, the magnitude of energy amplitude, a coefficient of such magnitude, and/or the magnitude of any coefficient related to energy at a particular frequency, frequency band, and/or frequency range. By way of non-limiting example, graph 21 depicts the frequency spectrum of an electroencephalographic (EEG) signal. Other signals related to brain activity are contemplated within the scope of this disclosure. As depicted in FIG. 2, the frequency spectrum is divided into four frequency bands: $\delta$ (delta) corresponds to the frequency band between 1-4 Hz, $\theta$ (theta) corresponds to the frequency band between 4-8 Hz, $\alpha$ (alpha) corresponds to the frequency band between 8-13 Hz, and $\beta$ (beta) corresponds to the frequency band between 13-30 Hz. Note that $\delta$, $\theta$, $\alpha$, and $\beta$ are measures of average or mean amplitude that correspond to the so-called delta band, theta band, alpha band, and beta band respectively. In some embodiments, frequency bands are continuous within their range, but this is not intended to be a limitation of this disclosure. In some embodiments, the different frequency bands may have no gaps there-between, but this is not intended to be a limitation of this disclosure. For example, the theta, alpha and beta band may range from 4-7 Hz, 8-12 Hz and 15-30 Hz, respectively. The depiction in FIG. 2 is intended as an exemplary embodiment, and not as a limitation of this disclosure. Some embodiments may use 2, 3, or more than 4 different frequency bands. The number of frequency bands used, or any upper and lower limits of any of the individual frequency bands used, as depicted or described herein, is merely exemplary and not intended as a limitation of this disclosure.

Returning to FIG. 1, electronic storage 130 of system 10 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store vectors of parameters based on the generated output signals, and/or other parameters (as discussed elsewhere herein), and/or other information. Electronic storage 130 may be a separate component within system 10, or electronic storage 130 may be provided integrally with one or more other components of system 10 (e.g., processor 110).

User interface 120 of system 10 in FIG. 1 is configured to provide an interface between system 10 and a user (e.g., a user 108, subject 106, a caregiver, a therapy decision-maker, etc.) through which the user can provide information to and receive information from system 10. This enables data, results, and/or instructions and any other communicable items, collectively referred to as "information," to be communicated between the user and system 10. An example of information that may be conveyed by user 108 to system 10 is patient-specific or subject-specific information related to a factor that is to be applied in determining the intensity of stimuli, such as the loudness of auditory stimuli. An example of information that may be conveyed to user 108 is a report detailing durations of and/or transitions between different sleep stages during a period of sleep or a period of monitoring subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Processor 110 of system 10 in FIG. 1 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of parameter determination module 111, control module 112, and/or other modules. Processor 110 may be configured to execute modules 111-112 by software; hardware; firmware; some combination of software, hardware, and/or firmware; and/or other mechanisms for configuring processing capabilities on processor 110.

It should be appreciated that although modules 111-112 are illustrated in FIG. 1 as being co-located within a single processing unit, in embodiments in which processor 110 includes multiple processing units, one or more of modules 111-112 may be located remotely from the other modules. The description of the functionality provided by the different modules 111-112 described herein is for illustrative purposes, and is not intended to be limiting, as any of modules 111-112 may provide more or less functionality than is described. For example, one or more of modules 111-112 may be eliminated, and some or all of its functionality may be incorporated, shared, integrated into, and/or otherwise provided by other ones of modules 111-112. Note that processor 110 may be configured to execute one or more additional modules that may perform some or all of the functionality attributed below to one of modules 111-112.

Parameter determination module 111 of system 10 in FIG. 1 is configured to determine one or more parameters from output signals generated by sensor(s) 142. The one or more parameters include a first spectral parameter, a second spectral parameter, a power parameter, and/or other parameters. The first spectral parameter indicates power (e.g. amplitude) in a first frequency band. For example, the first spectral parameter may indicate the mean amplitude of an EEG signal in the alpha band, as described above in relation to FIG. 2. In other words, alpha may be the first spectral parameter. The second spectral parameter indicates power in a second frequency band. For example, the second spectral parameter may indicate the mean amplitude of an EEG signal in the theta band, as described above in relation to FIG. 2. In other words, theta may be the second spectral parameter. In some embodiments, the first and second spectral parameters may be defined and/or determined such that the average frequency of the first frequency band of the first spectral parameter is higher than the average frequency of the second frequency band of the second spectral parameter, such as for the alpha band versus the theta band. In some embodiments, parameter determination module 111 is configured to determine a third, fourth, and/or additional spectral parameters in a manner similar to the first and second spectral parameters, though corresponding to other frequency bands. For example, parameter determination module 111 may determine delta and beta, as described above in relation to FIG. 2.

Returning to FIG. 1, parameter determination module 111 may be configured to determine a power parameter based on one or more spectral parameters. The power parameter may be referred to as "g" or "power parameter g". In some embodiments, power parameter g may be determined such that an increase in power and/or amplitude corresponding to relatively lower frequencies (e.g. delta and/or theta) and/or a decrease in power and/or amplitude corresponding to relatively higher frequencies (e.g. alpha and/or beta) correlates to an increase in power parameter g. Non-limiting examples are: $g=\alpha/\theta$, $g=\alpha-\theta$, $g=(\alpha+\beta)/(\delta+\theta)$, etc.

Figure 3:
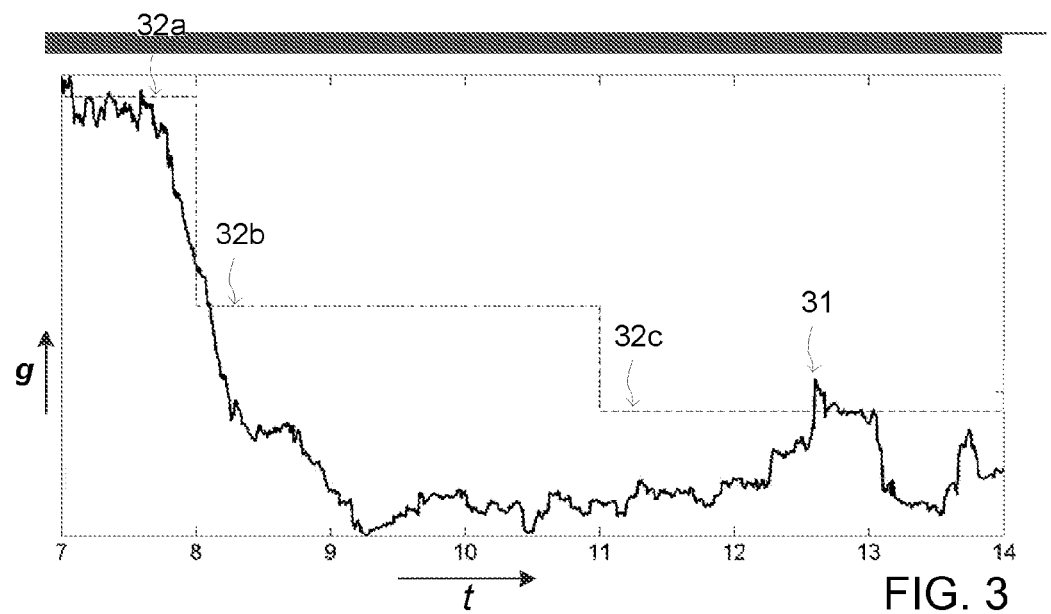
FIG. 3 illustrates a graph depicting changes over time in a power parameter based on changes in different frequency bands of brain activity.

By way of illustration, FIG. 3 illustrates a graph 31 depicting changes over time ("t" on the X-axis) in power parameter g ("g" on the Y-axis) based on changes in different frequency bands of brain activity. Time ranges from about 7 minutes after a subject started to attempt to fall asleep to about 14 minutes after the subject started to attempt to fall asleep. As depicted in the example in FIG. 3, $g=\alpha/\theta$. Recall that sleep onset is associated with various physiological changes, including a shift in brain activity amplitude distribution from higher frequencies to lower frequencies. In other words, as subject 106 is falling asleep, either relatively higher frequencies of brain activity decrease (e.g. $\alpha$ decreases), relatively lower frequencies of brain activity increase (e.g. $\theta$ increases), or both occur simultaneously. In either case, power parameter g will decrease correspondingly. As depicted here, the subject is falling asleep between 7 and 14 minutes after starting to attempt to fall asleep, and this correlates to the change in the value of power parameter g. Plateau 32a may correspond to a state of wakefulness. Plateau 32b may correspond to sleep stage N1. Plateau 32c may correspond to sleep stage N2. The determination of plateaus 32a-32c and/or the determination of the transitions between sleep stages may be based on observation, on an analysis of one or more physiological parameters, on an analysis of a (smoothed) vector of power parameter g that includes multiple samples, and/or on other factors and/or information. In some embodiments, such information may include expert assessment and/or identification of such plateaus, e.g. through sleep stage identification.

Returning to FIG. 1, operation of parameter determination module 111 may be performed in an ongoing manner, for example at a particular sampling period. The one or more parameters may be determined at different locations and/or positions within system 10 or near subject 106. In some embodiments, parameter determination module 111 may derive vectors of parameters in an ongoing manner during a period of monitoring subject 106. The vectors of the parameters may be based on vectors of generated output signals and/or other (vectors of) determined parameters.

Control module 112 is configured to control stimulus source 20 to deliver one or more stimuli to subject 106. The stimulus may be a sensory stimulus. The stimulus may include a series and/or sequence of stimuli. Controlling the stimulus may include controlling the intensity of one or more stimuli. Adjustments may be based on determined (spectral) parameters and/or generated output signals. For example, adjustments may be based on power parameter g. Adjustments may be made in an ongoing manner, for example at a particular sampling period. The rate of adjustment may be 0.5 second, 1 second, 2 seconds, 5 seconds, 10 seconds, 20 seconds, and/or another rate that is appropriate to provide feedback to subject 106 that is perceived as a (near immediate) response to efforts by subject 106 to modulate his/her brain activity. By virtue of measuring brain activity and delivering stimuli having an intensity that is based thereon, subject 106 may modulate his/her brain to promote similar physiological changes as occur naturally during sleep onset, thereby promoting and/or inducing faster onset of sleep.

In some embodiments a stimulus may include a short sound, such as a beep. The intensity of the sound may be the loudness of the sound. The intensity of subsequent deliveries of that short sound may be adjusted over time as described herein. In some embodiments, the one or more stimuli may include a long sound, such as a song. The intensity of the song may be the loudness of the song. The intensity of subsequent stimuli may be adjusted over time by adjusting the volume or loudness of the same song over time, as described herein. In other words, delivery of the song may be considered a delivery of multiple stimuli for the purposes of the described functionality of control module 112.

Adjustments by control module 112 may be based on a function that correlates power parameter g and the intensity of one or more delivered stimuli. Functions that are monotonically increasing or monotonically decreasing may be suitable to establish a predictable relation for (subject 106) between the intensity of the delivered stimuli and one or more spectral parameters (or a parameter derived therefrom such as power parameter g), including but not limited to linear, proportional, logarithmic, and/or other functions. In some embodiments, the function establishes a positive correlation.

Adjustments by control module 112 may be based on one or more subject-specific parameters and/or factors. In some embodiments, subject 106 may provide one or more preferences that may be taken into account by control module 112 during operation. For example, subject 106 may prefer very soft auditory stimuli. In some embodiments, subject 106 may require louder auditory stimuli. For example, through testing and/or calibration subject 106 may turn out to have poor hearing (also referred to as a high auditory perception threshold), thus requiring louder auditory stimuli.

In some embodiments, the connection between brain activity and delivering stimuli having a particular intensity may be used to prompt subject 106 to transition from a sleep stage into a state of wakefulness.

Figure 4:
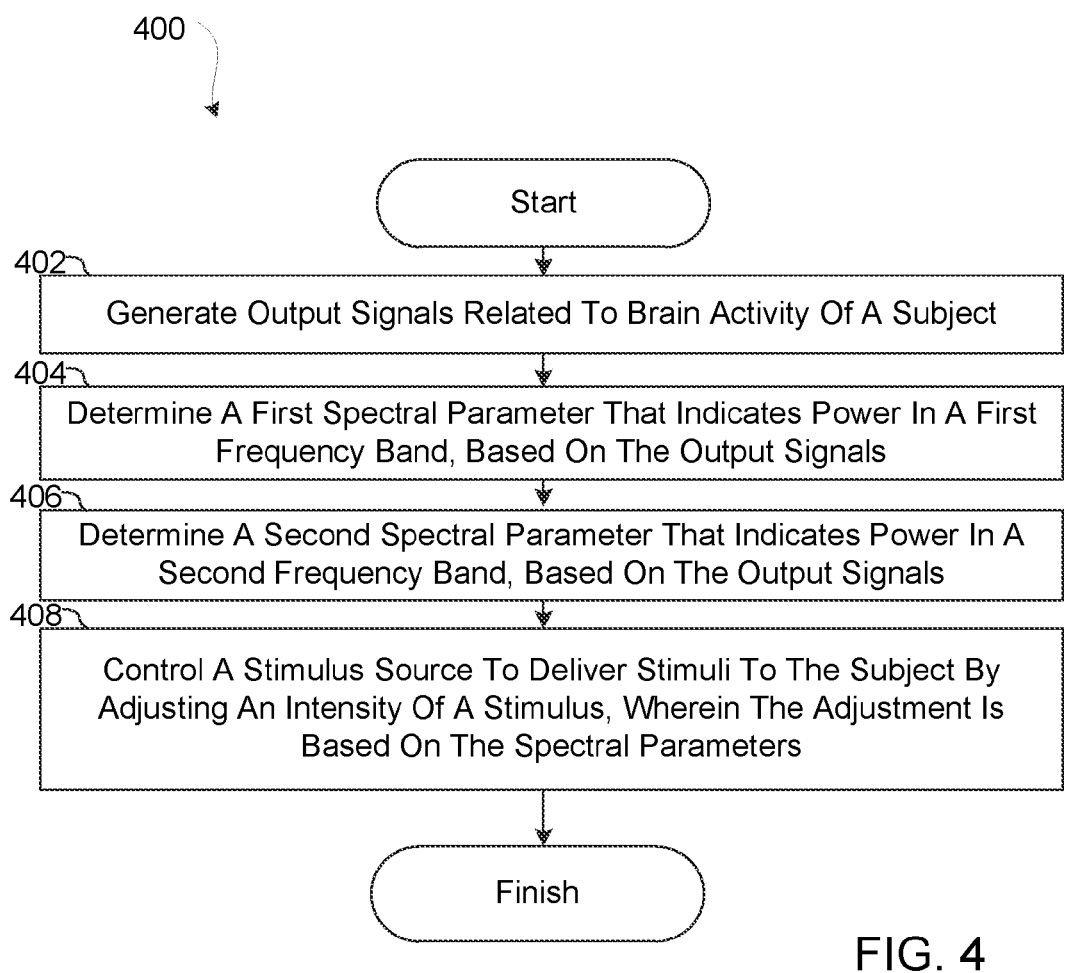
FIG. 4 illustrates a method to deliver stimuli to a subject that prompt the subject to transition into a sleep stage.

FIG. 4 illustrates a method 400 to deliver stimuli to a subject that prompt the subject to transition into a sleep stage. The operations of method 400 presented below are intended to be illustrative. In certain embodiments, method 400 may be accomplished with one or more additional operations not described, and/or without one or more of the operations discussed. Additionally, the order in which the operations of method 400 are illustrated in FIG. 4 and described below is not intended to be limiting.

In certain embodiments, method 400 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, one or more output signals are generated, the one or more output signals conveying information related to one or more parameters associated with brain activity of the subject. In some embodiments, operation 402 is performed by a sensor the same as or similar to sensor 142 (shown in FIG. 1 and described herein).

At an operation 404, a first spectral parameter is determined that indicates power in a first frequency band, wherein the first spectral parameter is based on the one or more generated output signals. In some embodiments, operation 404 is performed by a parameter determination module the same as or similar to parameter determination module 111 (shown in FIG. 1 and described herein).

At an operation 406, a second spectral parameter is determined that indicates power in a second frequency band, wherein the second spectral parameter is based on the one or more generated output signals. The average frequency of the first frequency band is higher than an average frequency of the second frequency band. In some embodiments, operation 406 is performed by a parameter determination module the same as or similar to parameter determination module 111 (shown in FIG. 1 and described herein).

At an operation 408, a stimulus source is controlled to deliver a stimulus to the subject by adjusting an intensity of the stimulus. The adjustment is based on the first spectral parameter and the second spectral parameter. In some embodiments, operation 408 is performed by a control module the same as or similar to control module 112 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

The invention claimed is:

1. A system configured to deliver stimuli to a subject that prompts the subject to transition into a sleep stage, the system comprising:
   one or more sensors configured to generate one or more output signals conveying information related to one or more parameters associated with brain activity of the subject;
   a tone generator configured to deliver an auditory stimulus to the subject; and
   one or more processors configured to execute computer program modules, the computer program modules comprising:
      a parameter determination module configured to determine a first spectral parameter that indicates power in a first frequency band and a second spectral parameter that indicates power in a second frequency band, wherein the first and second spectral parameters are based on the one or more generated output signals, wherein an average frequency of the first frequency band is higher than an average frequency of the second frequency band; and a control module configured to control the tone generator to adjust an intensity of the auditory stimulus, wherein the adjustment is based on the first spectral parameter and the second spectral parameter.

2. The system of claim 1, wherein one of the one or more output signals conveys information obtained through electroencephalography (EEG).

3. The system of claim 1, wherein the parameter determination module and the control module operate in an ongoing manner as the one or more sensors generate updated output signals, wherein the control module is configured such that decreasing the intensity of the auditory stimulus occurs in response to one or both of a decrease of the first spectral parameter and/or an increase of the second spectral parameter.

4. The system of claim 1, wherein the control module is further configured such that the intensity of the auditory stimulus is further based on a subject-specific factor, the subject-specific factor comprising an auditory perception threshold of the subject.

5. A method of controlling stimuli for delivery to a subject with a delivery system that prompts the subject to transition into a sleep stage, the delivery system comprising one or more sensors, a tone generator, and one or more processors configured to execute computer program modules, the modules comprising a parameter determination module and a control module, the method comprising:

generating with the one or more sensors, one or more output signals conveying information related to one or more parameters associated with brain activity of the subject;

delivering, with the tone generator, an auditory stimulus to the subject;

determining, with the parameter determination module, a first spectral parameter that indicates power in a first frequency band, wherein the first spectral parameter is based on the one or more generated output signals;

determining, with the parameter determination module, a second spectral parameter that indicates power in a second frequency band, wherein the second spectral parameter is based on the one or more generated output signals, and wherein an average frequency of the first frequency band is higher than an average frequency of the second frequency band; and controlling, with the control module, the tone generator to adjust an intensity of the auditory stimulus, wherein the adjustment is based on the first spectral parameter and the second spectral parameter.

6. The method of claim 5, wherein the one or more sensors are configured such that one of the one or more output signals conveys information obtained through electroencephalography (EEG).

7. The method of claim 5, wherein the one or more sensors are configured such that the step of generating one or more output signals is performed in an ongoing manner, and the control module is configured such that adjusting the intensity of the auditory stimulus includes decreasing the intensity of the auditory stimulus in response to one or both of a decrease of the first spectral parameter and/or an increase of the second spectral parameter.

8. The method of claim 5, wherein the control module is configured such that the adjusting of the intensity of the auditory stimulus is further based on a subject-specific factor, the subject specific factor comprising an auditory perception threshold of the subject.

9. A system configured to deliver stimuli to a subject that prompts the subject to transition into a sleep stage, the system comprising:

means for generating one or more output signals conveying information related to one or more parameters associated with brain activity of the subject;

means for delivering an auditory stimulus to the subject comprising a tone generator;

means for determining a first spectral parameter that indicates power in a first frequency band, wherein the first spectral parameter is based on the one or more generated output signals;

means for determining a second spectral parameter that indicates power in a second frequency band, wherein the second spectral parameter is based on the one or more generated output signals, and wherein an average frequency of the first frequency band is higher than an average frequency of the second frequency band; and means for controlling the means for delivering the auditory stimulus to the subject to adjust an intensity of the auditory stimulus, wherein the adjustment of the intensity of the auditory stimulus is based on the first spectral parameter and the second spectral parameter.

10. The system of claim 9, wherein one of the one or more output signals conveys information obtained through electroencephalography (EEG).

11. The system of claim 9, wherein the means for generating one or more output signals operates in an ongoing manner, and wherein the means for controlling the means for delivering the auditory stimulus is configured such that the intensity of the auditory stimulus is decreased in response to one or both of a decrease of the first spectral parameter and/or an increase of the second spectral parameter.

12. The system of claim 9, wherein the means for controlling the means for delivering the auditory stimulus is further configured such that adjustment of the intensity of the auditory stimulus is further based on a subject-specific factor, the subject-specific factor comprising an auditory perception threshold of the subject.

* * * * *